United States Patent
Tanaka (10) Patent No.: US 8,985,342 B2
(45) Date of Patent: Mar. 24, 2015

(54) COLOR SORTING MACHINE

(75) Inventor: Norihiko Tanaka, Tokyo (JP)

(73) Assignee: Satake Corporation, Tokyo (JP)

( * ) Notice: Subject to any disclaimer, the term of this patent is extended or adjusted under 35 U.S.C. 154(b) by 0 days.

(21) Appl. No.: 13/703,898

(22) PCT Filed: Jun. 2, 2011

(86) PCT No.: PCT/JP2011/062646
§ 371 (c)(1),
(2), (4) Date: Dec. 12, 2012

(87) PCT Pub. No.: WO2011/158656
PCT Pub. Date: Dec. 22, 2011

(65) Prior Publication Data
US 2013/0081982 A1    Apr. 4, 2013

(30) Foreign Application Priority Data
Jun. 18, 2010    (JP) ................. 2010-138808

(51) Int. Cl.
*B07C 5/00*    (2006.01)
*B07C 5/342*    (2006.01)
*B07C 5/36*    (2006.01)
*G01N 21/85*    (2006.01)

(52) U.S. Cl.
CPC ............. *B07C 5/3425* (2013.01); *B07C 5/366* (2013.01); *G01N 21/85* (2013.01)
USPC .......................................... 209/639; 209/580

(58) Field of Classification Search
USPC ......... 209/580, 581, 587, 638, 639, 644, 932, 209/938
See application file for complete search history.

(56) References Cited

U.S. PATENT DOCUMENTS

| | | | | |
|---|---|---|---|---|
| 6,100,488 A | * | 8/2000 | Satake et al. | 209/580 |
| 6,629,611 B2 | * | 10/2003 | Satake et al. | 209/657 |
| 2002/0008056 A1 | * | 1/2002 | Satake et al. | 209/657 |
| 2003/0094403 A1 | * | 5/2003 | Murata et al. | 209/581 |
| 2009/0283456 A1 | * | 11/2009 | Le Vot et al. | 209/644 |

FOREIGN PATENT DOCUMENTS

| | | |
|---|---|---|
| JP | 3044701 B2 | 2/1992 |
| JP | 2000-185263 A | 7/2000 |
| JP | 2001-050760 A | 5/2001 |
| JP | 2001-179186 A | 7/2001 |

(Continued)

*Primary Examiner* — Joseph C Rodriguez
*Assistant Examiner* — Kalyanavenkateshware Kumar
(74) *Attorney, Agent, or Firm* — Joseph P. Farrar, Esq.

(57) ABSTRACT

Provided is a color sorting machine in which decreases in yield resulting from the erroneous inclusion of good granules can be prevented by using different selection algorithms and operation ejector nozzle operations resulting therefrom in a first sorting part and a second sorting part. The machine is provided with: a binarization means for binarizing images of granular objects, a flaw-detecting means for extracting flawed parts of granular objects, a reducing means for reducing images of the external contour parts of granular objects, an enlarging means for enlarging images of the flawed parts of granular objects, and a synthesis means for synthesizing the reduced images of the external contours and the enlarged images of the flawed parts; wherein on the basis of an image obtained by this synthesis means, different air-jetting operations are established for the ejection means of a first sorting part and the ejection means of a second sorting part.

3 Claims, 6 Drawing Sheets

(56) References Cited

FOREIGN PATENT DOCUMENTS

| | | |
|---|---|---|
| JP | 2005-017190 A | 1/2005 |
| JP | 2001-083775 A | 3/2005 |
| JP | 2009-050760 A | 3/2009 |
| WO | WO 2009015486 A1 * | 2/2009 ............... B07C 5/34 |

* cited by examiner

COLOR SORTING MACHINE

BACKGROUND

1. Technical Field

The present invention relates to an apparatus for sorting out conforming granular objects from non-conforming granular objects by color.

2. Background Art

There is well known a color sorting machine which projects light onto objects to be sorted (granular objects) serving as a material, senses the difference between the amount of light from each object to be sorted and the amount of light of a background that serves as a reference with, e.g., an optical sensor, and screens out granular objects without a predetermined color (a predetermined amount of light) with an ejector, such as an air injection nozzle, on the basis of detection signals from the optical sensor. Among the screened-out granular objects without the predetermined color are some normal granular objects (conforming grains). For this reason, a secondary sorting unit which picks out conforming grains from among granular objects discharged through a non-conforming grain outlet is generally provided to improve the rate of screening. The rate of screening refers to the ratio of the total weight of non-conforming grains mixed in granular objects separated and fed to a non-conforming grain port to the total weight of non-conforming grains mixed in granular objects as a material.

Figure 6:
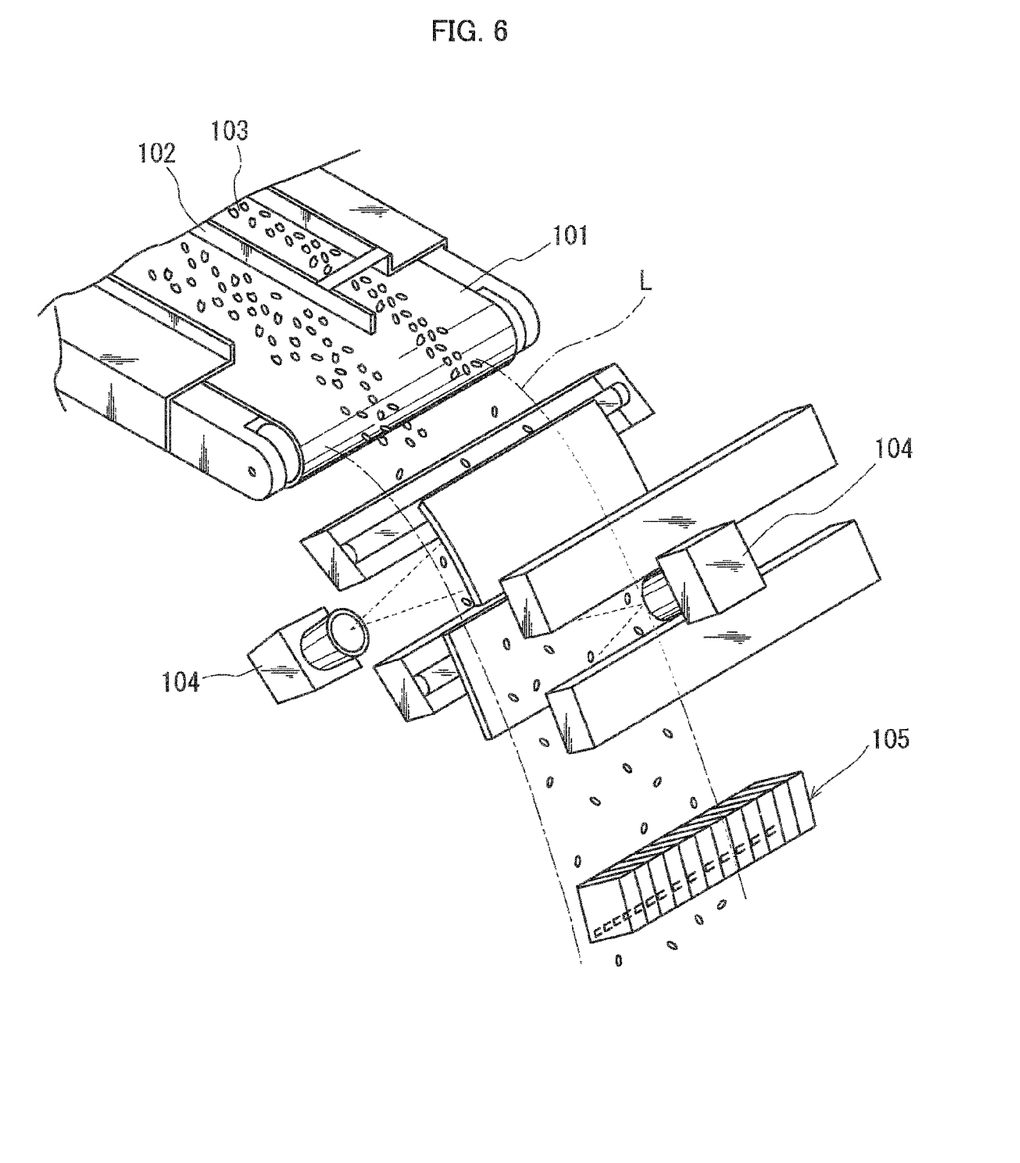
FIG. 6 is a perspective view of a conventional color sorting machine using a belt conveyor.

As shown in simplified form in FIG. 6 of the present application, Japanese Patent No. 3044701 discloses a granular object color sorting machine in which a conveying surface 101 of a belt conveyor is divided by a partition wall 102 to form a conveying surface 103 for secondary sorting, a vibrating supply trough for secondary sorting (a feeder not shown), a detection unit 104, and an ejector 105 are provided, comparators having positive reference voltages (threshold values) are provided in a control unit for primary sorting and secondary sorting, respectively, and switches are respectively provided to output or stop signals from the comparators.

With the above-described configuration, primary sorting and secondary sorting are performed in parallel by supplying granular objects removed by primary sorting and separately fed to a non-conforming grain outlet to the conveying surface 103 for secondary sorting formed by the partition wall 102 on the belt conveyor. If there are a small number of normal grains (conforming grains) among the granular objects removed by primary sorting and separately fed to the non-conforming grain outlet, in secondary sorting, the current reference voltage is switched and set to a reference voltage opposite in polarity to one in primary sorting by a switch, and the conforming grains smaller in number than non-conforming grains are removed by the ejector (reverse screening).

The disclosed color sorting machine can set a positive reference voltage or a negative reference voltage according to the rate of mixed non-conforming grains in primary sorting and secondary sorting, use different screening sensitivities for primary sorting and secondary sorting, or set "reverse screening" described above in secondary sorting.

However, the use of different screening sensitivities in a primary sorting unit and a secondary sorting unit and setting of "reverse screening" in the secondary sorting unit cannot be said to be a fundamental solution to a reduction in yield. More specifically, in the primary sorting unit of the color sorting machine, the rate of non-conforming grains mixed in granular objects separated and fed to a conforming grain side is low. In other words, the primary sorting unit removes non-conforming grains without fail with an emphasis on the quality of granular objects separated and fed to the conforming grain side and thus often screens out and removes conforming grains together with non-conforming grains. Similarly, the secondary sorting unit often screens out and removes conforming grains together with non-conforming grains. The rate of conforming grains mixed in non-conforming grains increases, which leads to a declining trend in yield. The cause of the trend will be described with reference to FIGS. 7A and 7B.

Figure 7A:
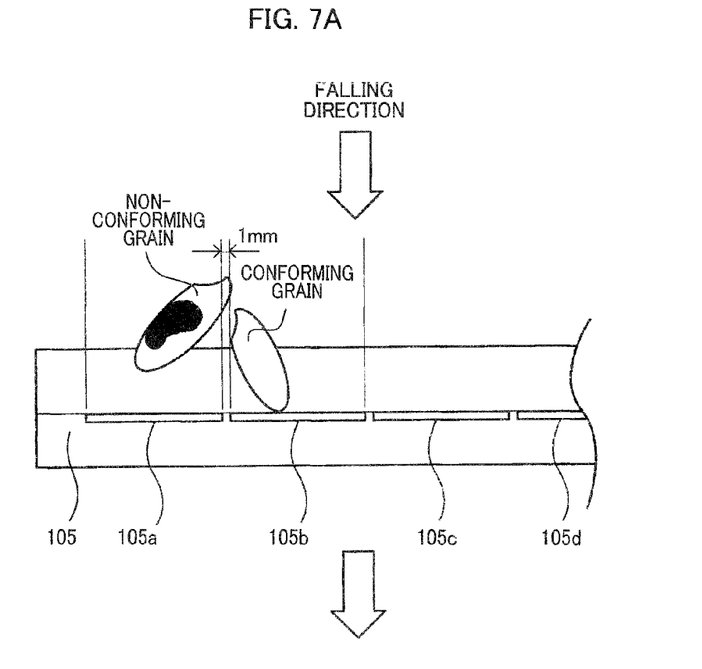
FIG. 7A is a schematic explanatory view showing air injection from an ejector nozzle and involvement of a conforming grain in separation of a non-conforming grain.
Figure 7B:
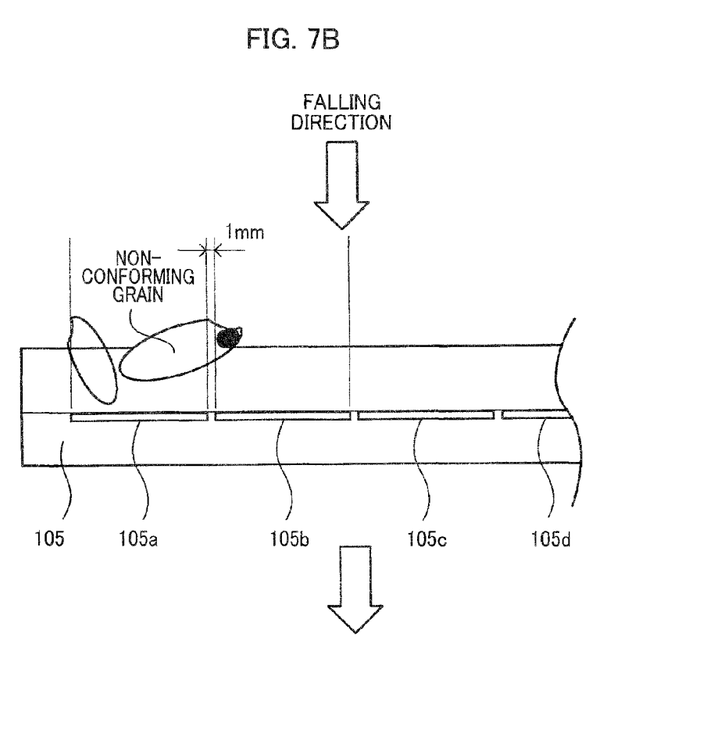
FIG. 7B is a schematic explanatory view showing air injection from the ejector nozzle and involvement of a conforming grain in separation of a non-conforming grain.

FIGS. 7A and 7B show the ejector 105 in a multi-channel color sorting machine. A gap between two adjacent air injection nozzle ports 105a and 105b is formed to be as narrow as about 1.0 mm. As shown in FIG. 7A, the conventional color sorting machine is set so as to simultaneously operate the two air injection nozzle ports of the air injection nozzle port 105a and the air injection nozzle port 105b in proximity to a conforming grain to inject air and remove a non-conforming grain in order to prevent a failure to remove the non-conforming grain when the non-conforming grain in proximity to the conforming grain passes near the air injection nozzle port 105a. This leads to a declining trend in yield. If only the one air injection nozzle port 105b is operated when a non-conforming grain passes astride the two air injection nozzle ports 105a and 105b, as in FIG. 7B, air cannot be injected to a center position (barycentric position) of the non-conforming grain, and a failure to remove (eliminate) the non-conforming grain occurs. The color sorting machine is thus set so as to prevent a failure in removal by simultaneously operating the two air injection nozzle ports, i.e., the air injection nozzle port 105a together with the air injection nozzle port 105b to inject air to the center position (barycentric position) of the non-conforming grain. However, if a conforming grain is passing on the air injection nozzle port 105a side at the time of the simultaneous operation, the conforming grain is involved in the removal of the non-conforming grain and is also removed. This leads to a declining trend in yield.

SUMMARY OF INVENTION

In consideration of the above-described problem, the present invention has as its technical object to provide a color sorting machine capable of inhibiting a conforming grain from being involved in separation of a non-conforming grain and being separated together with the non-conforming grain and consequently reducing yield by setting a primary sorting unit and a secondary sorting unit so as to be different in both sorting algorithm and ejector nozzle operation.

In order to solve the above-described problem, the present invention takes the technical measures below in a color sorting machine including a primary sorting unit including transport means for primary sorting for letting granular objects serving as a material flow down in the form of a belt, an optical detection unit provided along a fall path for a granular object falling down from the transport means, and ejector means provided below the optical detection unit for removing primary non-conforming grains from among normal granular objects, a secondary sorting unit including transport means for secondary sorting for letting the primary non-conforming grains removed by the primary sorting unit flow down in a plurality of rows, an optical detection unit provided along a fall path for a granular object falling down from the transport means, and ejector means provided below the optical detection unit for removing a secondary non-conforming grain from the primary non-conforming grains, and ejector operation determination means.

The technical measures are that the optical detection units in the primary sorting unit and the secondary sorting unit include binarization means for binarizing an image of a granular object obtained through imaging, defect detection means for extracting an image of a defective part of the granular object from the image obtained by the binarization means, outline detection means for extracting an image of an outline part of the granular object from the image obtained by the binarization means, erosion means for eroding an image of an outline part obtained by the binarization means, dilation means for dilating the image of the defective part obtained by the defect detection means, and merging means for merging the eroded image of the outline part obtained by the erosion means and the dilated image of the defective part obtained by the dilation means and that the ejector operation determination means makes air injection operation of the ejector means for the primary sorting unit and air injection operation of the ejector means for the secondary sorting unit different, regarding operation of the ejector means that operate on the basis of an image obtained by the merging means.

More specifically, the ejector operation determination means causes the ejector means for the primary sorting unit to operate an air injection nozzle port which is to remove a primary non-conforming grain concerned and an adjacent air injection nozzle port and causes the ejector means for the secondary sorting unit to operate only an air injection nozzle port which is to remove a secondary non-conforming grain concerned.

In the invention according to claim 2, the erosion means performs four-neighbors erosion on an image of an outline part of a granular object obtained by the primary sorting unit at least once and performs transverse erosion on an image of an outline part of a granular object obtained by the secondary sorting unit a plurality of times.

In the invention according to claim 3, the dilation means performs eight-neighbors dilation on an image of a defective part of a granular object obtained by the primary sorting unit a plurality of times and performs eight-neighbors dilation on an image of a defective part of a granular object obtained by the secondary sorting unit a plurality of times.

In the invention according to claim 4, the color sorting machine further includes center position calculation means for calculating a center position in a falling direction of the granular object on the basis of an image obtained by the erosion means.

Advantageous Effects of Invention

According to the color separating machine of the present invention, an image of a granular object picked up by imaging means, such as a CCD camera, which is provided inside each optical detection unit is binarized with a predetermined threshold value, and the defect detection means counts the number of pixels in a black part of the binarized image and determines whether the granular object has a defective part. The erosion means erodes a binarized image of an outline part of the granular object to generate the eroded image. Since the outline part in the image is eroded toward a center position of the grain, settings can be made so as to operate only an air injection nozzle port located in an area closest to the center position of the grain. Additionally, the dilation means dilates a binarized image of a defective part of the granular object to generate an dilated image. With this configuration, the defective part can be incorporated into the eroded image of the outline part such that the defective part is highlighted.

In other words, a position of the granular object is recognized in relation to an air injection nozzle port on the basis of the eroded image of the outline part obtained by the erosion means, and whether the granular object is a non-conforming grain is determined on the basis of the dilated image of the defective part.

The merging means merges the eroded image of the outline part and the dilated image of the defect image by a well-known method, such as an addition, a subtraction, or a multiplication. The ejector operation determination means performs processing in which air injection operation of the ejector means for the primary sorting unit and air injection operation of the ejector means for the secondary sorting unit are different, such as simultaneously operating an air injection nozzle port which is to remove a primary non-conforming grain and an adjacent air injection nozzle port in primary sorting and operating only an air injection nozzle port which is to remove a secondary non-conforming grain in secondary sorting, on the basis of an image obtained by the merging. This allows screening with an emphasis on quality that can prevent omission of removal of a non-conforming grain in the primary sorting unit and screening with an emphasis on increase in yield that prevents a conforming grain from being involved in separation of a non-conforming grain and being separated together with the non-conforming grain in the secondary sorting unit.

In the invention according to claim 2, the erosion means performs four-neighbors erosion on an image of an outline part of a granular object obtained by the primary sorting unit at least once and performs transverse erosion on an image of an outline part of a granular object obtained by the secondary sorting unit a plurality of times. In the primary sorting unit, the load of image processing can be reduced. In contrast, in the secondary sorting unit, an outline of an image of a non-conforming grain is eroded toward a center position of the grain, a barycentric position of the granular object moves toward a center in a width direction of an air injection nozzle port on a picture, and an ejector to be operated is clearly determined. Accordingly, only non-conforming grains can be properly removed with accuracy.

In the invention according to claim 3, the dilation means performs eight-neighbors dilation on an image of a defective part of a granular object obtained by the primary sorting unit a plurality of times and performs eight-neighbors dilation on an image of a defective part of a granular object obtained by the secondary sorting unit a plurality of times. This allows a defective part of a granular object to be highlighted such that information on the defective part is not lost due to erosion of an image of an outline part of the granular object.

In the invention according to claim 4, the color sorting machine further includes center position calculation means for calculating a center position in a falling direction of the granular object on the basis of an image obtained by the merging means. It is thus possible to calculate a center position O of a non-conforming grain with simple processing and properly remove non-conforming grains with accuracy.

DETAILED DESCRIPTION OF THE EMBODIMENT

Figure 1:
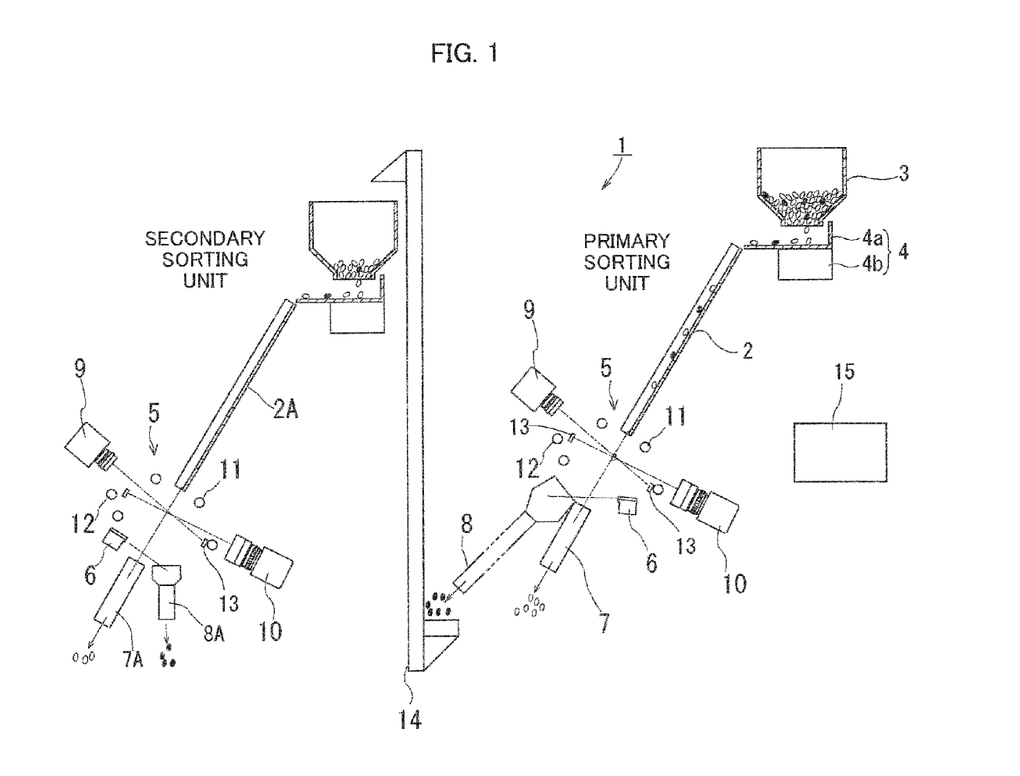
FIG. 1 is a schematic view of a color sorting machine according to an embodiment of the present invention.

An embodiment of the present invention will be described with reference to the drawings. FIG. 1 is a schematic view of a color sorting machine according to the embodiment of the present invention. A color sorting machine 1 in FIG. 1 can receive grains of cereals, resin pellets, beans, and other granular objects as a material and sort out conforming grains from non-conforming grains or foreign objects and the like mixed in the material by color. The color sorting machine 1 includes a primary sorting unit and a secondary sorting unit which are provided in parallel, and components for a color sorting machine which are similar to those of a conventional color sorting machine are arranged in each sorting unit.

Components of the primary sorting unit will be described. The primary sorting unit includes a chute 2 as transport means which is arranged so as to be inclined at an angle of about 60° with respect to a horizontal position, a storage tank 3 for storing granular objects such as grains of cereals, a vibrating feeder 4 for conveying a granular object from the storage tank 3 to the chute 2, an optical detection unit 5 which is provided such that a flow-down path of a granular object flowing down from a lower end of the chute 2 is sandwiched between components on two sides, an ejector nozzle 6 which is provided below the optical detection unit 5, a primary conforming grain discharge pipe 7 located below the ejector nozzle 6 and on the same inclined line as the chute 2 which receives a granular object in the flow-down path without air injection from the ejector nozzle 6, and a primary non-conforming grain discharge pipe 8 for collecting a non-conforming grain among normal granular objects with air injection from the ejector nozzle 6.

The chute 2 for the primary sorting unit is preferably in the shape of a flat plate without a groove for causing granular objects to slide in the form of a wide belt. A chute cover may be provided at a predetermined distance from a bottom surface in order to prevent granular objects from overflowing the chute 2 or prevent a granular object to be sorted from coming off from the bottom surface while sliding on the chute 2.

In the vibrating feeder 4, a feeder trough 4a is supported on a support unit 4b. A granular object can be supplied to the chute 2 by operating a vibrating device such as an electromagnetic actuation coil.

As the optical detection unit 5, an optical sensor unit which is composed of a CCD camera 9 for visible light, a NIR camera 10 for near-infrared light, and the like, a visible light source 11 which is composed of, e.g., a fluorescent lamp, a near-infrared light source 12 which is composed of, e.g., a halogen lamp, and a facing background 13 for the optical sensor unit are disposed.

Reference numeral 14 denotes an elevating machine for supplying non-conforming grains screened out by the primary sorting unit to the secondary sorting unit for re-sorting.

Components of the secondary sorting unit will be described. The difference from the primary sorting unit lies in the shape of a chute 2A. The chute 2A for secondary sorting has a plurality of grooves for causing granular objects to slide separately in a plurality of rows (multiple rows). A U-shape, a V-shape, a rectangular shape, or the like can be appropriately adopted as the cross-sectional shape of the grooves. The secondary sorting unit includes a secondary conforming grain discharge pipe 7A located below the ejector nozzle 6 and on the same inclined line as the chute 2A which receives a granular object in a flow-down path without air injection from the ejector nozzle 6 and a secondary non-conforming grain discharge pipe 8A for collecting a non-conforming grain from among normal granular objects with air injection from the ejector nozzle 6. The other components are substantially the same as those of the primary sorting unit.

Reference numeral 15 denotes a control unit for determining on the basis of image data obtained by the optical detection unit 5 whether a granular object is a conforming one or a non-conforming one, performing arithmetic processing, and controlling the color sorting machine. As for the specific configuration of the control unit, the control unit is preferably composed of an electronic computer, such as a computer, and may be composed of input means, such as a keyboard or a mouse, a CPU which performs computation, determination, image processing, and the like, a storage device (e.g., a RAM, a ROM, or a hard disk drive) for storing an operating program for operating the color sorting machine 1 and editing image data, and the like. Drive units and the like of the vibrating feeders 4, the CCD cameras 9, the NIR cameras 10, the visible light sources 11, the near-infrared light sources 12, and the ejector nozzles 6 are electrically connected to the control unit 15. The control unit 15 controls the units.

<Concerning Image Processing Unit Included in Control Unit>

Figure 2:
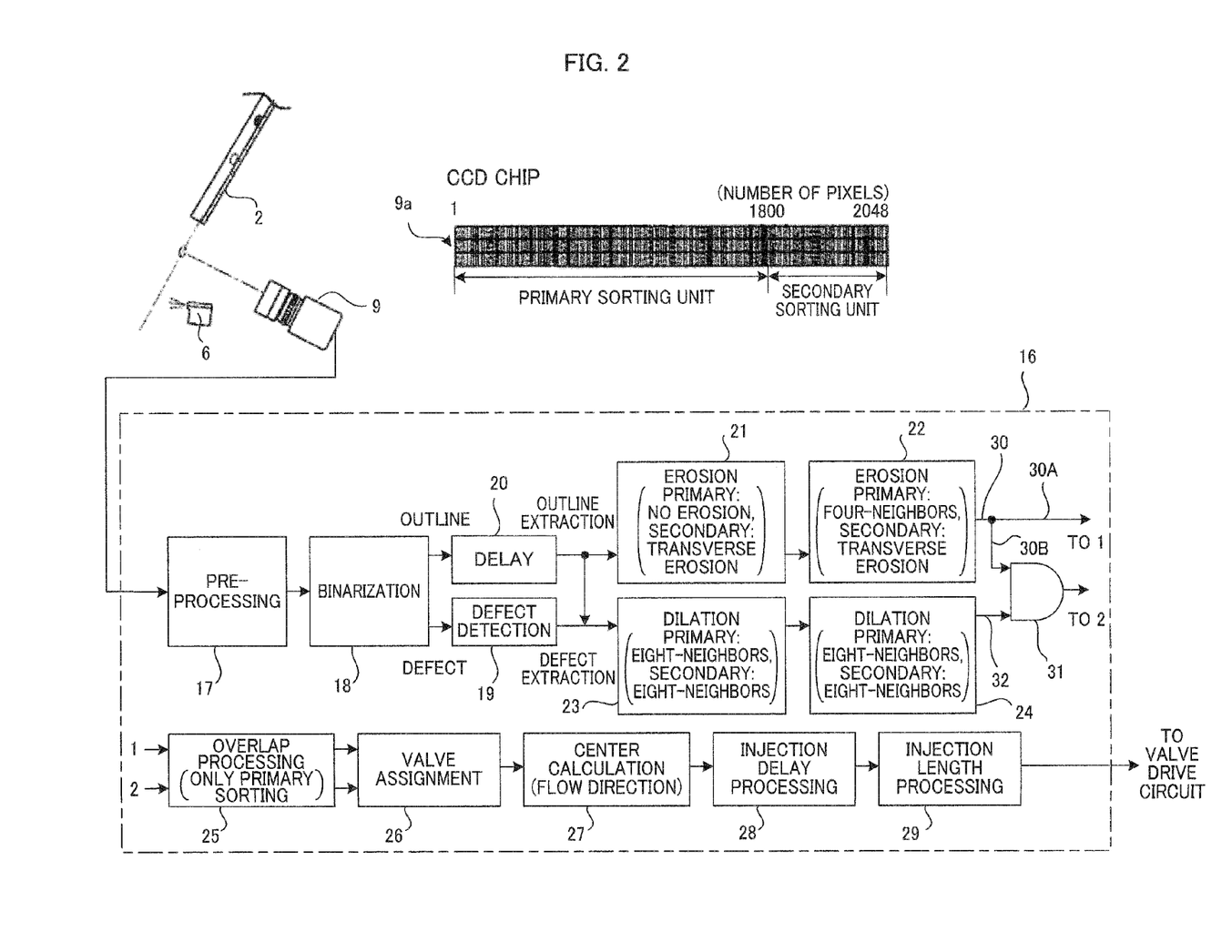
FIG. 2 is a block diagram of an image processing unit included in a control unit of the color sorting machine of the present invention.

FIG. 2 is a block diagram of an image processing unit 16 included in the control unit 15. A main portion of the image processing unit 16 is composed of a pre-processing unit 17 which synchronizes an image from the CCD camera 9 or the like and performs shading correction on the image obtained under biased illumination, a binarization unit 18 which binarizes the corrected image, a defect detection unit 19 which counts pixels of a black part of the binarized image and, if pixels, the number of which is not less than a predetermined threshold value, are detected, determines that a defective part is present in a granular object, a delay circuit 20 for timing adjustment for the defect detection unit 19, a first erosion unit 21 which erodes a binarized image including an extracted outline part of the granular object, a second erosion unit 22 which further erodes the image eroded by the first erosion unit 21, a first dilation unit 23 which dilates a binarized image including an extracted defect of the granular object, a second dilation unit 24 which further dilates the image dilated by the first dilation unit 23, an overlap processing unit 25 which decides to simultaneously bring two air injection nozzle ports of an air injection nozzle port corresponding to the grain with the defective part and an adjacent air injection nozzle port into air injection operation on the basis of the images, a valve assignment unit 26 which generates signals for turning on/off valves of the ejector nozzle, a center position calculation unit 27 which calculates a center position of the granular object in a falling direction of the granular object, an injection delay (delay time) processing unit 28, and an injection length (injection time) processing unit 29. Note that ejector operation determination means in the present invention refers to a combination of the overlap processing unit 25 and the valve assignment unit 26.

As shown in FIG. 2, a CCD element composed of a CCD chip 9a is provided inside the CCD camera 9. The CCD chip 9a has a total of 2048 pixels in a horizontal direction and is formed such that first to 1800th pixels monitor the primary sorting unit (a width direction of the chute 2 of flat plate shape) while 1801st to 2048th pixels monitor the secondary sorting unit (a width direction of the multi-channel chute 2A with the plurality of grooves). Since divided pixel areas are provided for the primary sorting unit and secondary sorting unit, the primary sorting unit and secondary sorting unit can perform different image processes.

<Concerning Binarization>

Figure 3:
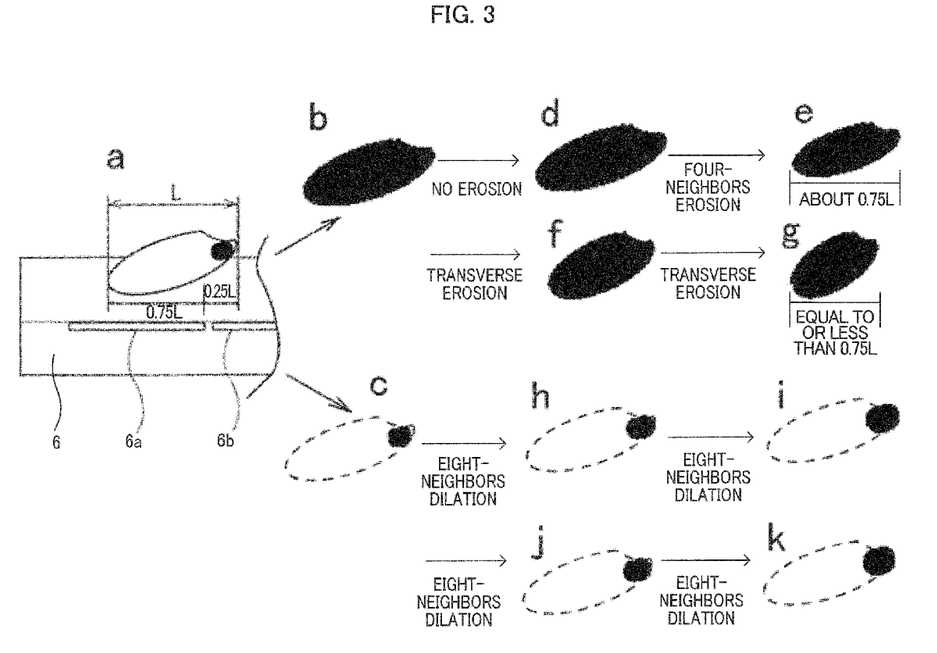
FIG. 3 is a conceptual diagram of an original image obtained by a CCD camera and conversion of the original image by the image processing unit.

FIG. 3 shows a conceptual diagram of an original image obtained by the CCD camera 9 or the like and various images into which the original image is converted by the image processing unit 16. Reference character a in FIG. 3 shows how a non-conforming grain having a defective part shown in black passes astride air injection nozzle ports 6a and 6b of the ejector nozzle 6. Let L be the length (the length in a width direction of the ejector nozzle 6) of the non-conforming grain. The length of a part on the air injection nozzle port 6a side accounts for 75% of the overall length L while a part protruding from the air injection nozzle port 6a accounts for 25% of the overall length L.

The non-conforming grain has already been imaged by the CCD camera 9 installed on the upstream side before reaching the air injection nozzle ports 6a and 6b. An image obtained by the imaging is given as an original image (the image a in FIG. 3) to the image processing unit 16, and the pre-processing unit 17 synchronizes the image and performs shading correction on the image obtained under biased illumination.

The image corrected by the pre-processing unit 17 is input to the binarization unit 18. The binarization unit 18 binarizes the image to separately produce an outline part and a defective part using an outline threshold value associated with pixel brightness and a defective part threshold value associated with brightness which is different from the outline threshold value. More specifically, if the original image is as indicated by reference character a in FIG. 3, for example, the outline part is generated as indicated by reference character b in FIG. 3 from the binarized original image using the outline threshold value while the defective part is generated as indicated by reference character c in FIG. 3 from the binarized original image using the defective part threshold value. This allows outline extraction and defect extraction of the non-conforming grain.

<Concerning Erosion of Outline Part>

A binarized image of the outline part generated by the binarization unit 18 is sequentially fed to the first erosion unit 21 and second erosion unit 22 and is repeatedly subjected to erosion a plurality of times. At this time, the primary sorting unit and secondary sorting unit are set so as to be different in the number of times of erosion and erosion method.

TABLE 1

|  | Erosion (for the 1st time) | Erosion (for the 2nd time) |
| --- | --- | --- |
| Primary sorting | No erosion | four-neighbors erosion |
| Secondary sorting | Transverse erosion | Transverse erosion |

Figure 5A:
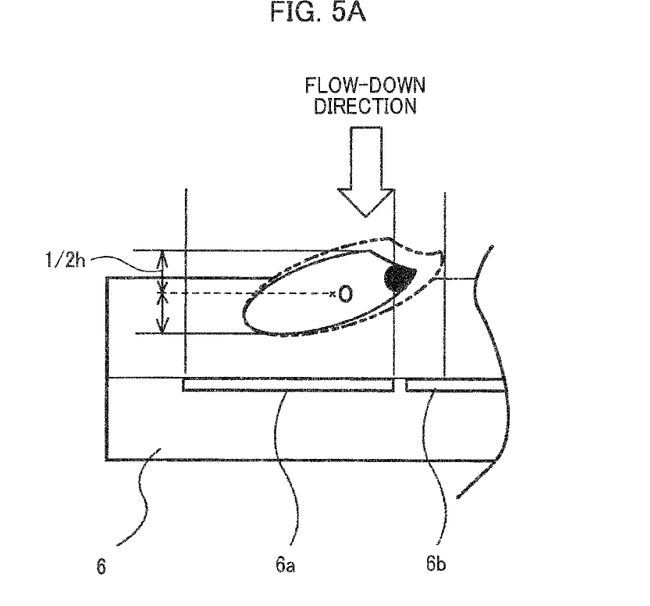
FIG. 5A is a conceptual view of calculation of a center position of a grain after image processing.

If the primary sorting unit and secondary sorting unit are set so as to be different in the number of times of outline port erosion and erosion method, as in Table 1, the load of image processing can be reduced in the primary sorting unit while an image of an outline part of a non-conforming grain is eroded toward a center position of the grain in the secondary sorting unit to allow settings to be made so as to operate only an air injection nozzle port corresponding to an area closest to the center position of the grain. Reference character d in FIG. 3 denotes an image which is obtained without subjecting a binarized image obtained by the primary sorting unit to erosion in the first erosion unit 21, and reference character e in FIG. 3 denotes an image which is obtained by subjecting the binarized image obtained by the primary sorting unit to four-neighbors erosion (erosion in four directions of upward, downward, left, and right directions (four-neighbors)) in the second erosion unit 22. With this sequence, the image e in FIG. 3 has been reduced to about the same size as an area occupied by the air injection nozzle port 6a (the overall length L of the grain has been reduced to 75%) with respect to the image a in FIG. 3 as the original image, and only the air injection nozzle port 6a corresponding to the area closest to the center position of the non-conforming grain is operated (FIG. 5A).

Figure 5B:
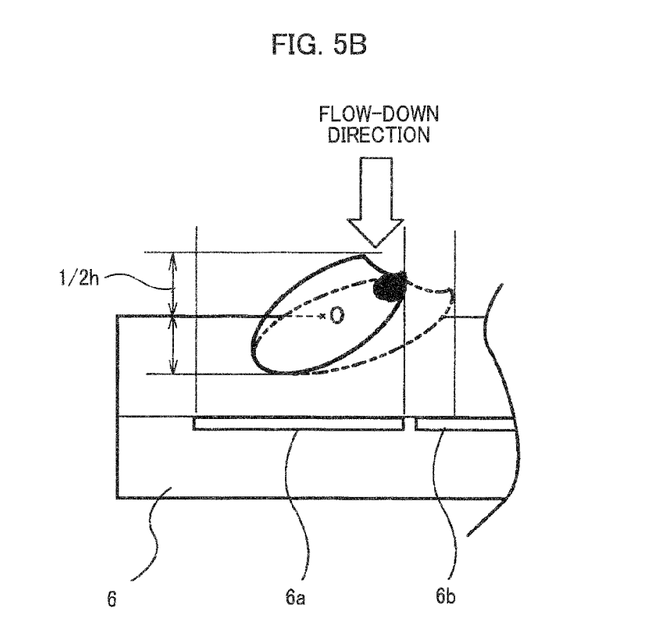
FIG. 5B is a conceptual view of calculation of a center position of a grain after image processing.

Reference character f in FIG. 3 denotes an image which is obtained by subjecting a binarized image obtained by the secondary sorting unit to transverse erosion (erosion in two directions of left and right directions) in the first erosion unit 21, and reference character g in FIG. 3 denotes an image which is obtained by further subjecting the image to transverse erosion in the second erosion unit 22. With this sequence, the image g in FIG. 3 has been made smaller than the area occupied by the air injection nozzle port 6a (the overall length L of a grain is not more than 75%) with respect to the image a in FIG. 3 as an original image, which allows settings to be made so as to operate only the air injection nozzle port 6a corresponding to an area closest to a center position of a non-conforming grain (FIG. 5B).

<Concerning Dilation of Defective Part>

A binarized image of the defective part generated by the binarization unit 18 is sequentially fed to the first dilation unit 23 and the second dilation unit 24 and is repeatedly subjected to dilation a plurality of times. At this time, the primary sorting unit and secondary sorting unit are preferably set so as to be the same in the number of times of dilation and dilation method.

TABLE 2

|  | Dilation (for the 1st time) | Dilation (for the 2nd time) |
| --- | --- | --- |
| Primary sorting | eight-neighbors dilation | eight-neighbors dilation |
| Secondary sorting | eight-neighbors dilation | eight-neighbors dilation |

If the primary sorting unit and secondary sorting unit are set so as to be the same in the number of times of defective part dilation and dilation method, as in Table 2, an image of a defective part after dilation can be easily incorporated into an image of an outline part after the above-described erosion (the image e or the image g in FIG. 3). Additionally, although erosion of an outline part of a granular object is performed twice in the secondary sorting unit, as in Table 1, and information on a defective part at an edge of the outline part may be lost, a defective part of a non-conforming grain can be highlighted by performing dilation of an image of the defective part twice, as in Table 2. Reference character h in FIG. 3 denotes an image which is obtained by subjecting a binarized image of a defective part obtained by the primary sorting unit to eight-neighbors dilation (dilation in eight directions of upward, downward, left, and right and diagonal directions (eight-neighbors)) in the first dilation unit 23, and reference character i in FIG. 3 denotes an image which is obtained by further subjecting the image to eight-neighbors dilation in the second dilation unit 24. Similarly, reference character j in FIG. 3 denotes an image which is obtained by subjecting a binarized image of a defective part obtained by the secondary sorting unit to eight-neighbors dilation in the first dilation unit, and reference character k in FIG. 3 denotes an image which is obtained by further subjecting the image to eight-neighbors dilation in the second dilation unit 24.

<Concerning Merging of Outline Part and Defective Part>

The image processing unit 16 will be described again with reference to FIG. 2. An outline image output line 30 from the second erosion unit 22 branches off into an input line 30A which is input to the overlap processing unit 25 and an input line 30B which is input to an AND circuit 31. A defect image output line 32 from the second dilation unit 24 is input to the AND circuit 31. In the AND circuit 31, an outline image and a defect image are merged by a well-known method, such as a multiplication (AND operation). Reference character b in FIG. 4 denotes an illustration obtained by merging an outline part image denoted by reference character e in FIG. 3 and a defective part image denoted by reference character i in FIG. 3, and reference character d in FIG. 4 denotes an illustration obtained by merging an outline part image denoted by reference character g in FIG. 3 and a defective part image denoted by reference character k in FIG. 3. The plurality of composite images and outline part images are input to the overlap processing unit 25. Processing in which air injection operation of ejector means for the primary sorting unit and air injection operation of ejector means for the secondary sorting unit are different (screening algorithms are different), as in Table 3 below, is performed. This allows screening with an emphasis on quality that can prevent omission of removal of a non-conforming grain in the primary sorting unit and screening with an emphasis on increase in yield that prevents a conforming grain from being involved in separation of a non-conforming grain and being separated together with the non-conforming grain in the secondary sorting unit. Respective roles can be assigned between the primary sorting and the secondary sorting.

TABLE 3

| | Overlap processing |
|---|---|
| Primary sorting | Performed |
| Secondary sorting | Not performed |

<Concerning Center Position Calculation Unit>

Figure 4:
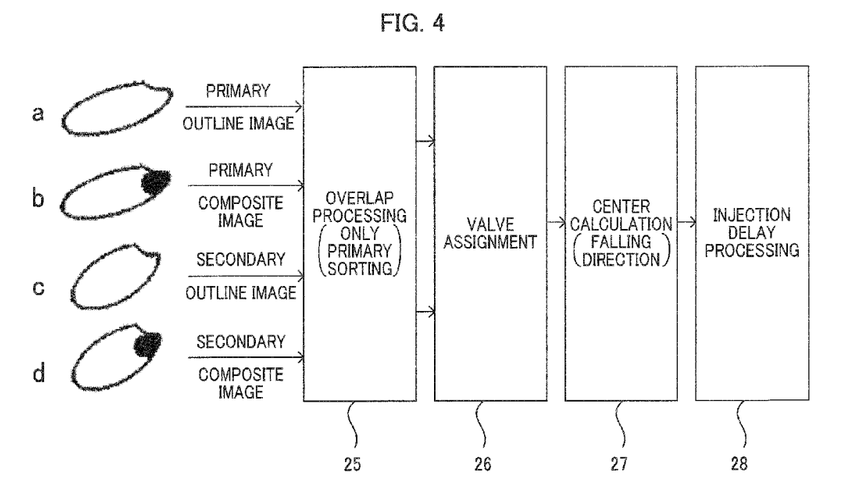
FIG. 4 is a conceptual diagram of input of image data obtained by merging an image of an outline part and an image of a defective part to an overlap processing unit.

As shown in FIG. 4, an output signal from the overlap processing unit 25 is input to the center position calculation unit 27 through the valve assignment unit 26. The center position calculation unit 27 calculates a distance h from a front edge to a rear edge of a non-conforming grain in a falling direction of the grain (see FIGS. 5A and 5B) and calculates one-half of the distance. At this time, a length L in a transverse direction (the width direction of the chute 2 or the width direction of the ejector nozzle 6) of the non-conforming grain is made to fit within the width dimension of the ejector nozzle 6 by the above-described image processing, and the length L in the transverse direction of the non-conforming grain need not be calculated. This simplifies a process of calculating a center position O of the non-conforming grain.

<Concerning Air Injection and Removal>

An output signal from the center position calculation unit 27 is input to the injection length (injection time) processing unit 29 through the injection delay (delay time) processing unit 28 (see FIG. 2). The injection delay processing unit 28 performs control so as to inject air according to the fall time of a non-conforming grain falling between the optical detection unit 5 and the ejector nozzle 6, and the injection length processing unit 29 controls the air injection time of the ejector nozzle 6. With this configuration, removal of non-conforming grains can be properly performed with accuracy. As shown in FIG. 5A, in the primary sorting unit, an original image indicated by a broken line is image-processed in a manner as indicated by a solid line by erosion of an outline part and dilation of a defective part. More specifically, the defective part protruding into the air injection nozzle port 6b in an adjacent lane in the original image moves toward the air injection nozzle port 6a in a lane where a center position O of a non-conforming grain is present, and the air injection nozzle port 6a that covers the center position O of the non-conforming grain can be operated. As shown in FIG. 5B, in the secondary sorting unit, an original image indicated by a broken line is image-processed in a manner as indicated by a solid line by erosion of an outline part and dilation of a defective part. More specifically, the defective part protruding into the air injection nozzle port 6b in an adjacent lane in the original image moves toward the air injection nozzle port 6a in a lane where a center position O of a non-conforming grain is present, and the air injection nozzle port 6a that covers the center position O of the non-conforming grain can be operated. Since transverse erosion is performed twice in the secondary sorting unit, the degree to which the defective part moves toward the air injection nozzle port 6a in the lane where the center position O of the non-conforming grain is present is large. It is thus possible to calculate a center position of a non-conforming grain with accuracy and properly remove only non-conforming grains with accuracy.

As has been described above, a conventional color sorting machine is intended to improve the quality of granular objects classified as conforming grains and adopts an overlap system which operates a plurality of air injection nozzle ports of an air injection nozzle port which is to remove a non-conforming grain and an adjacent air injection nozzle port in both of a primary sorting unit and a secondary sorting unit. For this reason, even a conforming grain is removed due to involvement in separation of a non-conforming grain, which leads to a declining trend in yield. In contrast, according to the present embodiment, an air injection nozzle port which is to remove a primary non-conforming grain and an adjacent air injection nozzle port are operated in the primary sorting unit while only an air injection nozzle port which is to remove a secondary non-conforming grain is operated in the secondary sorting unit. Accordingly, in the primary sorting unit, grains that are suspected to be non-conforming grains, such as a colored grain, are all removed by air injection in order to prevent omission of removal of a non-conforming grain. In the secondary sorting unit, an image of an outline part of a non-conforming grain is eroded toward a center position of the grain, and only an air injection nozzle port corresponding to an area closest to the center position of the grain is operated to property remove only the non-conforming grain with accuracy. This configuration prevents a conforming grain from being involved in separation of a non-conforming grain to reduce yield.

Note that a color sorting machine according to the present invention is not limited to the above-described embodiment and that the configuration may, of course, be appropriately changed without departing from the scope of the present invention. For example, a color sorting machine including a primary sorting unit, a secondary sorting unit, and a tertiary sorting unit can be configured such that the sorting units are set so as to be different in air injection operation and screening algorithm.

In the above-described embodiment, a non-conforming grain is separated by injection in secondary sorting. However, a granular object to be separated can be changed to a conforming grain by, for example, inverting a reference voltage for sorting out non-conforming grains from conforming grains from positive to negative. This method is suitable when there are a small number of conforming grains among granular objects to be subjected to secondary sorting (granular objects on the non-conforming grain side obtained as a result of primary sorting).

INDUSTRIAL APPLICABILITY

The present invention provides a color sorting machine with a rate of screening out non-conforming grains which is improved as a result of the configuration below. The color sorting machine uses different screening algorithms for primary sorting and secondary sorting. In primary sorting, screening is performed so as to prevent, to the utmost, non-conforming grains from being mixed while permitting involvement of a conforming grain in separation of a non-conforming grain. In secondary sorting that further sorts granular objects fed to a non-conforming grain side by primary sorting, only non-conforming grains are screened out with accuracy while involvement of a conforming grain in separation of a non-conforming grain is avoided.

The invention claimed is:

1. A color sorting machine for sorting out a conforming granular object from a non-conforming granular object by color, comprising:
a primary sorting unit including transport means for primary sorting for letting granular objects serving as a material flow down in the form of a belt, an optical detection unit provided along a fall path for a granular object falling down from the transport means, and ejector means provided below the optical detection unit for removing primary non-conforming grains from among normal granular objects;
a secondary sorting unit including transport means for secondary sorting for letting the primary non-conforming grains removed by the primary sorting unit flow down in a plurality of rows, an optical detection unit provided along a fall path for a granular object falling down from the transport means, and ejector means provided below the optical detection unit for removing a secondary non-conforming grain from the primary non-conforming grains; and
ejector operation determination means including an overlap processing unit and a valve assignment unit,
wherein the optical detection units in the primary sorting unit and secondary sorting unit include:
binarization means for binarizing an image of a granular object obtained through imaging;
defect detection means for extracting an image of a defective part of the granular object from the image obtained by the binarization means;
outline detection means for extracting an image of an outline part of the granular object from the image obtained by the binarization means;
erosion means for eroding the image of the outline part extracted by the outline detection means;
dilation means for dilating the image of the defective part obtained by the defect detection means; and
merging means for merging the eroded image of the outline part obtained by the erosion means and the dilated image of the defective part obtained by the dilation means, and
the ejector operation determination means causes the ejector means for the primary sorting unit to execute an air injection operation that simultaneously operates multiple adjacent air injection nozzle ports at positions corresponding to a position of a primary non-conforming grain and causes the ejector means for the secondary sorting unit to execute an air injection operation that operates only a single air injection nozzle port at a position corresponding to a position of a secondary non-conforming grain, on the basis of an image obtained by the merging means,
wherein the erosion means performs four-neighbors erosion on the image of the outline part of the granular object at least once for the primary sorting unit and performs transverse erosion on the image of the outline part of the granular object a plurality of times for the secondary sorting unit,
wherein the primary sorting unit and the secondary sorting unit perform different processes, with the primary sorting unit configured to conduct overlap processing and the secondary sorting unit configured to not perform overlap processing.

2. The color sorting machine according to claim 1, wherein the dilation means performs eight-neighbors dilation on the image of the defective part of the granular object a plurality of times for both the primary and secondary sorting units.

3. The color sorting machine according to claim 1, comprising center position calculation means for calculating a center position in a falling direction of the granular object on the basis of the image obtained by the erosion means.

* * * * *